United States Patent
Hofmann

(10) Patent No.: US 11,027,220 B2
(45) Date of Patent: Jun. 8, 2021

(54) CHROMATOGRAPHY COLUMNS AND PROCESSES

(71) Applicant: BIOTECHFLOW LTD, Stroud (GB)

(72) Inventor: Martin John Hofmann, Stroud (GB)

(73) Assignee: BIOTECHFLOW LTD

(*) Notice: Subject to any disclaimer, the term of this patent is extended or adjusted under 35 U.S.C. 154(b) by 0 days.

(21) Appl. No.: 16/587,268

(22) Filed: Sep. 30, 2019

(65) Prior Publication Data

US 2020/0023289 A1    Jan. 23, 2020

Related U.S. Application Data

(63) Continuation of application No. 15/074,017, filed on Mar. 18, 2016, now abandoned.

(51) Int. Cl.

| *B01D 15/18* | (2006.01) |
|---|---|
| *B01D 15/22* | (2006.01) |
| *B01D 15/26* | (2006.01) |
| *C07K 1/22* | (2006.01) |
| *G01N 30/56* | (2006.01) |
| *G01N 30/60* | (2006.01) |

(52) U.S. Cl.
CPC ......... *B01D 15/1807* (2013.01); *B01D 15/22* (2013.01); *B01D 15/265* (2013.01); *C07K 1/22* (2013.01); *G01N 30/6004* (2013.01); *G01N 30/56* (2013.01); *G01N 30/6017* (2013.01)

(58) Field of Classification Search
CPC .. B01D 15/1807; B01D 15/22; B01D 15/265; C07K 1/22; G01N 30/56; G01N 30/6004; G01N 30/6017
See application file for complete search history.

(56) References Cited

U.S. PATENT DOCUMENTS 5,169,522 A * 12/1992 Shalon ................... B01D 15/08
                                                          210/198.2

FOREIGN PATENT DOCUMENTS

WO    WO-9610451 A1 *  4/1996    ............. F16K 1/446

* cited by examiner

*Primary Examiner* — Latosha Hines
(74) *Attorney, Agent, or Firm* — Dureska & Moore, LLC; David P. Dureska; David J. Danko

(57) ABSTRACT

A separation column for expanded bed adsorption comprises a column tube (2), a base (15) carrying an inlet rotor structure (6) for pumping in process liquid, and a top cap (3). The top cap (3) is conical in form, and has a peripheral flange 31 by which it is rigidly fixed to the top edge flange (22) of the column tube (2). The angle of the convergent interior surface (35) of the conical top cap (3) may be between 10 and 25°. A vortex-inhibitor component (8) projects down below the outlet structure (4) at the top of the cap, projecting into the operating space (15) of the column to inhibit rotation of liquid in the column interior. An expanded bed adsorption process is done with upward flow of liquid in the column through a bed of media particles.

19 Claims, 2 Drawing Sheets

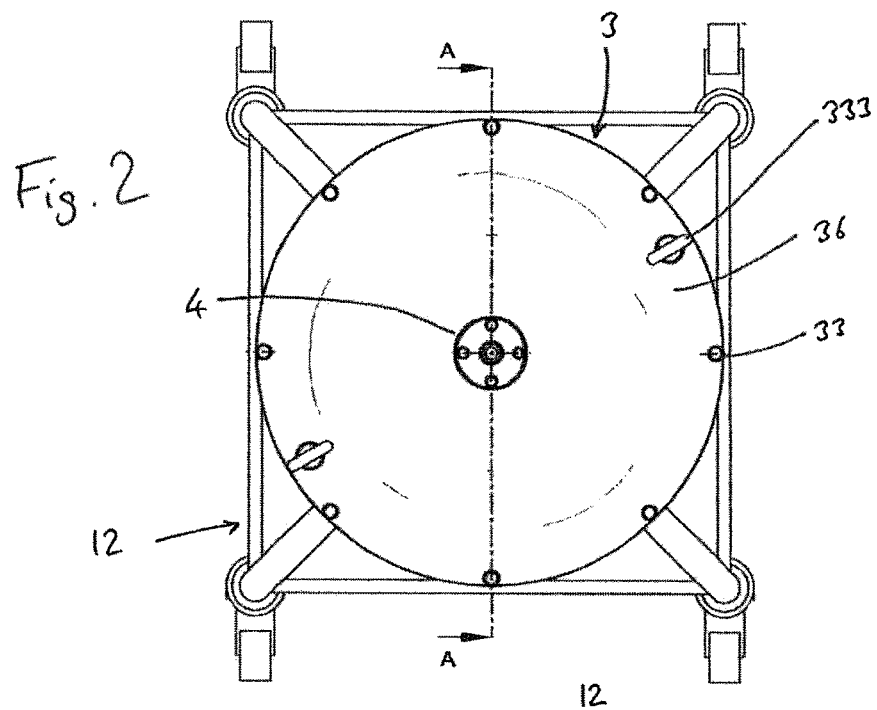
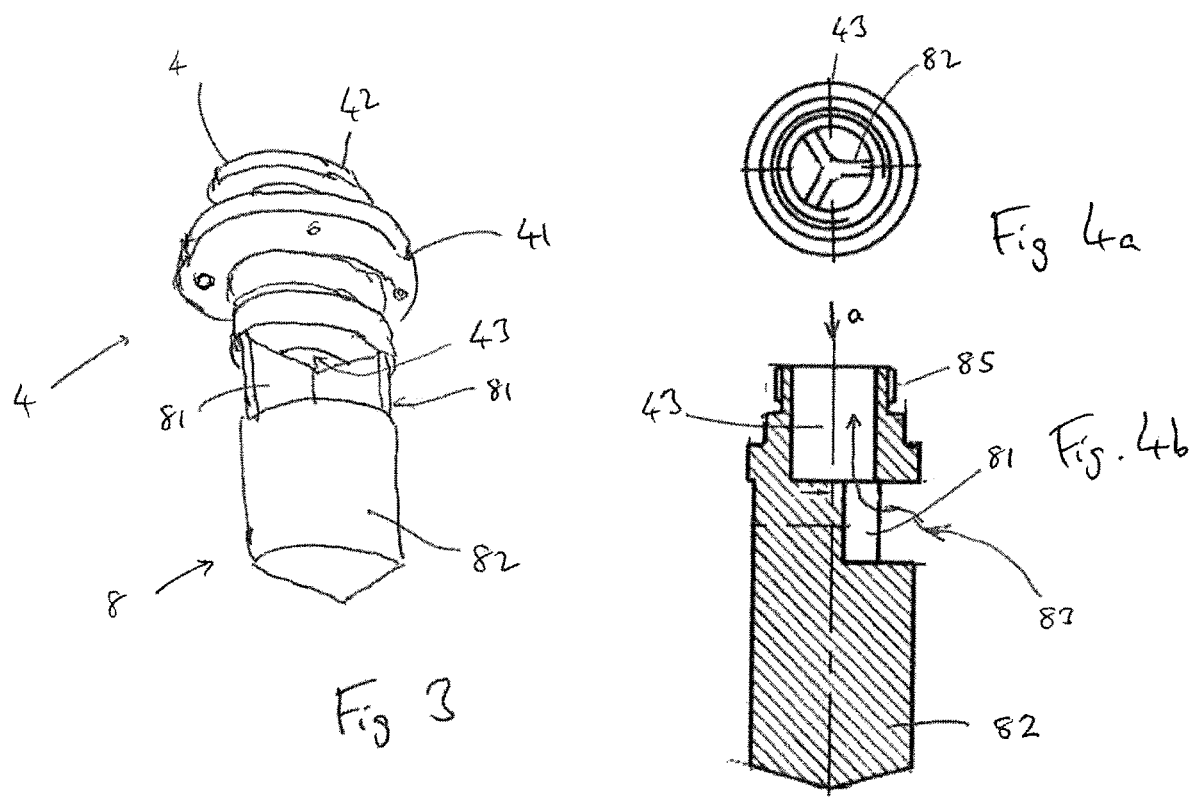

CHROMATOGRAPHY COLUMNS AND PROCESSES

CROSS-REFERENCE TO RELATED APPLICATIONS

This application is a continuation of U.S. patent application Ser. No. 15/074,017 filed Mar. 18, 2016, which claims the benefit of United Kingdom Patent Application No. 1504695.6 filed Mar. 19, 2015.

FIELD OF THE INVENTION

This invention relates to apparatus and methods for separation of substances by chromatography, particularly but not exclusively expanded-bed chromatography.

BACKGROUND

Expanded bed or fluidised bed separation processes (often known as EBA: "expanded bed adsorption") are well known. They are useful for example in the production of biologically-produced molecules e.g. for drugs, vaccines, diagnostic agents or the like. Many such products are produced in cell cultures and they (or their precursors) must be separated from a culture product such as a homogenised broth or slurry which contains insoluble solids such as cell debris as well as contaminants. This solid material cannot pass through a conventional packed (fixed bed) chromatography column to adsorb the product chromatographically in conventional preparative chromatography. The solids would block and contaminate the system. Rather, the culture product must first be clarified, i.e. processed by filtration and/or centrifugation to remove the solid matter and create a process liquid able to pass through a packed phase bed. Expanded bed procedures offer the separation of target components from such process liquids without the necessity for preliminary clarification or separation of solids by centrifugation or filtration, or at least with a reduced need for this.

In expanded bed processes a bed of adsorbent medium particles is provided in a column and subjected to an up-flow of liquid which expands or fluidises the bed of particles. The bed reaches a predetermined height and stabilises with a clear or supernatant space above the particles and below an outlet. The process liquid containing the substance(s) to be separated, and which may contain solid matter, is injected into the bottom of the column and passes up through the expanded bed to an outlet. Unlike packed columns, mesh retainers are not required at the top or bottom of the column, although they may be used especially at the bottom. The outlet may be an open conduit such as a downwardly-projecting pipe. Solid material in the process liquid can pass right up through the bed to the outlet and escape. Target product is generally adsorbed onto the particles of the bed and can subsequently be eluted (washed) from it.

A feature of expanded bed processes is the need to maintain the expanded bed of particles in a stable and effective state, avoiding direct channelling of liquid through the bed. If this cannot be achieved reliably, the process is not industrially viable.

Our WO2014/125304 describes columns suitable for expanded bed adsorption having a special self-aligning top piston structure incorporating an outlet conduit, enabling reduced height of the system compared with the previous ones. These columns work well and are easy to use. Nevertheless, the apparatus is relatively complex, with plural moving parts and seals.

THE INVENTION

The aim herein is to provide novel apparatus useful in separation and chromatography methods, especially expanded bed adsorption, and offering simplicity and convenience.

In a first aspect the invention provides separation apparatus comprising a column tube defining an internal volume or operating space to contain a bed of particles in use. The apparatus has an outlet structure of a bottom inlet structure for the passage of process liquid. A fixed cap component at the top of the apparatus has an upwardly convergent inner surface or flow surface facing onto the operating space, and provides the outlet structure, usually centrally. The cap component is fixed to the column tube side wall around a peripheral fixing portion of the cap component. Preferably this fixing is by bolts or other threaded fasteners, although other fixings such as clamps may be used.

Preferably the cap component is fixed around a top edge of the column tube side wall.

Preferably the cap component has a downwardly-directed fitting surface, desirably a radial surface, which fits against an upwardly-directed fitting surface, preferably a radial surface, of the column tube side wall, preferably at the top edge thereof as mentioned. The cap component may fit only against the top exterior of the tube or tube flange without projecting down inside the column or contacting outwardly against its interior surface. That is, the flow/liquid contacting surface of the column tube may terminate at the top of the column tube. Additionally or alternatively however the cap component or a portion thereof may fit down or plug down inside the column wall and have a radially outwardly directed surface facing or engaging against the interior of the column tube side wall.

The interior convergent flow surface of the top cap component contacts liquid in the column in use, guiding liquid flow from the column towards the outlet structure. It is preferably convergent from the periphery substantially to the outlet structure. The periphery of the convergence is desirably at the diameter of the column tube. The convergence is desirably conical. Preferably a single conical surface extends substantially from the periphery to the outlet structure. The angle of convergence, e.g. the angle or angles of the or each mentioned conical surface, or the angle defined by a notional conical surface between the peripheral fixing portion (at its inward extremity bordering on the operating space) and the outlet structure periphery is desirably between 4 degrees and 25 degrees, more preferably between 10 degrees and 25 degrees, more preferably 15 degrees to 20 degrees. For example there may be a single conical surface with an angle between 4 degrees and 30 degrees, more preferably between 10 degrees and 25 degrees, more preferably 15 degrees to 20 degrees.

The skilled person will appreciate that the angle can be selected readily in dependence on the process to be run, taking into account e.g. the expected flow velocity, the material of the surface and the adhesive tendency of any process materials (such as cell debris) or air bubbles thereto, to ensure that the liquid flow progressively clears the surface during the process. Plural cap components with different flow surface shapes and/or angles may be provided which can be fitted to the same column tube for different process conditions.

The cap component may consist essentially of a single conical piece with peripheral fixings for the column tube side wall and a central outlet structure. It may be of metal e.g. stainless steel, or of plastics material such as polypropylene, or of some combination of these.

It will be understood that in the normal way, deformable seal members such as one or more elastomer rings may be provided acting between the opposed fitting surfaces of the cap component and column tube side wall.

The outlet structure preferably is (or comprises) a structure fixed in the top cap component. It may comprise a discrete conduit component fixed, e.g. bolted or directly threaded, into the top cap component. It may be a simple tube. More preferably it comprises, incorporates or mounts a formation for inhibiting rotational flow (that is, rotation around the axis of the column tube). Such a formation may be provided as or comprising one or more vanes. One or more vanes extending both axially and in the radial direction is/are preferred, such as two or more vanes projecting radially (or substantially radially) out from the axis and mounted in the outlet opening of the outlet structure and/or projecting below the level of the flow surface of the fixed cap component down into the operating volume. Such structures divide the flow entering the outlet opening, and inhibit rotational movement.

We also find that a downwardly-directed axial baffle or nose portion, preferably at or below the level of one or more vanes as proposed above, helps to inhibit fluid rotation. This may be by promoting approach of fluid towards the outlet radially inwardly from the periphery, rather than from the axial direction. An independent beneficial effect of a projecting nose component can be to occupy a space below the outlet opening in which, if it were fluid-filled, a vortex could otherwise tend to stabilise. That is to say, the nose portion can inhibit vortex formation by projecting into or impinging on a potential vortex formation region e.g. an axial region enclosed by the top cap component.

These measures are found to reduce the liability of the flow system to the formation of vortices and other fluid flow phenomena which can disrupt an expanded particle bed, and especially when a rotary inlet is used for process fluid input at the bottom of the column tube.

We find that the mentioned structure ("vortex inhibitor") desirably reaches substantially down as far as the axial position where the fixed cap component begins to converge, e.g. at least 80% of that distance, more preferably at least 90% or 100% of that distance. The vortex inhibitor may be provided in a single fitting which may be attached at or to the underside of the cap component, or is incorporated wholly or partly in it.

The inlet structure for the column tube is not particularly limited, and may be especially any inlet structure known to be used for expanded bed separation processes, but we prefer that it comprises an array of process liquid injection holes distributed over or across a floor of the column tube. Particularly preferably the apparatus comprises a process liquid injection rotor mounted rotatably at the bottom of the column tube, and having a plurality of arms with a corresponding plurality of liquid injection holes. Desirably the holes are downwardly directed.

As mentioned, with expanded bed processes it is desirable to maintain stability and uniformity within the expanded bed and for this reason distribution of the injected liquid (which may or may not include process sample liquid incorporating the substance(s) to be separated, in addition to process liquid feed for fluidising or expanding the particle bed) is desirably distributed across the cross-section of the column tube.

These input rotors are known to the skilled person, and have significant known advantages, but they sometimes tend to initiate vortex formation in the operating space; the rotation direction can be reversed from time to time to alleviate this, but this is one reason why a vortex inhibitor at the top of the column tube, provided with the present fixed cap component, can be advantageous. In fact, even without a rotary structure at the process liquid input, there is a tendency for vortex formation where liquid flows from the large cross-section of the column tube to the restricted cross-section of the outlet conduit, especially via the convergent flow surface of the top cap. Accordingly there can be a complementary interaction between the flow components of the system. The top vortex inhibitor is found effective to reduce vortex formation without need for any mesh or flow-regulating structure spanning the column above the bed, and indeed need not be at the bottom of the bed either, and this is advantageous because these structures are liable to fouling and may cause channelling which is inimical to effective EBA.

Another aspect of the invention is a separation process carried out in apparatus according to any of the present proposals, in which a process liquid is caused to flow up through the column tube of the apparatus, from the inlet structure to the outlet structure, through a bed of a particulate medium causing expansion of the bed, accompanied by separation of a target substance from the process liquid (usually by adsorption onto the media particles). Usually the process comprises a subsequent stage of separating target substance from the medium, typically by elution done in the column tube.

The process liquid may comprise a cell culture product, such as a broth, slurry or homogenised or otherwise process broth or slurry which may contain insoluble solids. Desirably the process operates with process liquid completely filling the operating space, and at the top of the apparatus flowing radially inwardly over the convergent flow face of the fixed cap component from the periphery of the column tube to the outlet structure. As is well known in an expanded bed process, the top of the bed is usually stabilized at a bed level below the top of the column tube, or below the top of the convergent flow face, with a generally clear, particle-free or supernatant liquid-filled region above the bed.

The proposed structure of the column top offers significant and practical advantages. Firstly, being fixed, it is much simpler to operate the column than with a piston. The column tube and fixed cap can be designed with a size and shape (e.g. convergence angle) appropriate to an intended process. There is no need to control the height of the piston, adjust the position of an outlet conduit, or manoeuvre heavy components. Especially when the fitting surfaces of the cap component and side wall are respectively downward and upward as described, an effective and easily energisable seal is made easily and directly, and the cap component may simply fit in the manner of a lid onto the top edge of the column tube wall. The cap can be removed easily for cleaning, directly exposing all the operational surfaces at the top of the column tube.

By making the internal and external shape of the cap component generally conformal, the thickness and hence the weight of this can be kept low. Depending on the size and pressure rating of the apparatus, the cap component may be either machined, pressed, moulded or some combination of these.

In preferred embodiments the column tube wall is wholly or partially transparent to facilitate monitoring the process within.

BRIEF DESCRIPTION OF THE DRAWINGS

By way of illustration, an embodiment of the invention is now described with reference to the accompanying drawings in which:

FIG. 2 is a planned view of the column (with the inlet conduit removed);

FIG. 3 shows an outlet structure including a vortex inhibitor, and

FIGS. 4*a* and 4*b* are a top end view and an axial cross-section of the vortex inhibitor.

DETAILED DESCRIPTION OF THE EMBODIMENT

Figure 1:
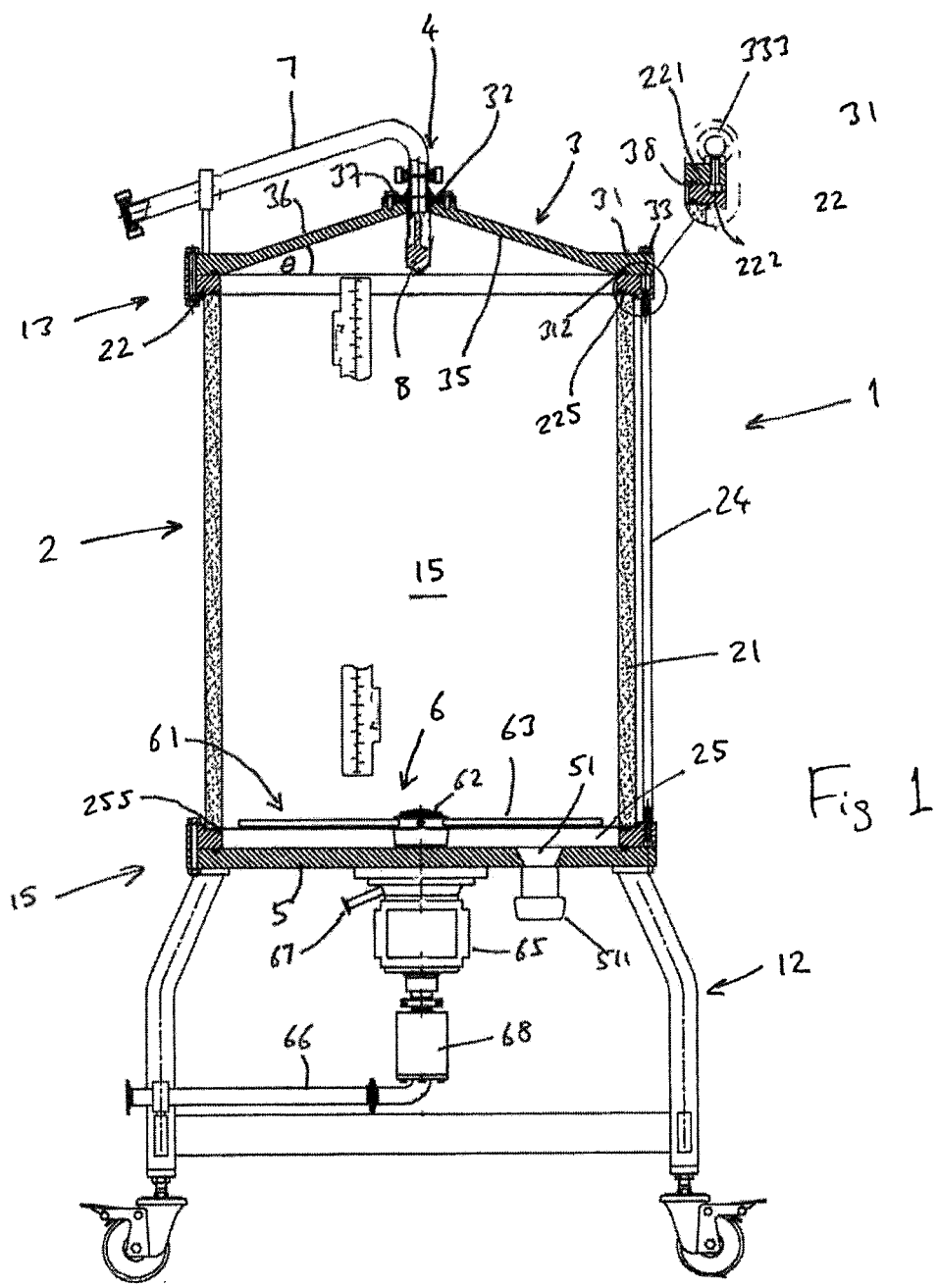
FIG. 1 is a vertical axial cross-section through an expanded bed separation column embodying the invention, taken at A-A shown in FIG. 2.

The separation apparatus 1 in this embodiment is an expanded bed separation column with a column tube 2. In this example the column tube is 600 mm in internal diameter. It has a cylindrical tube side wall 21 made of transparent acrylic 40 mm thick, held between an annular metal top flange 22 at the top 13 of the apparatus and an annular metal bottom flange 25 at the base 15. The base 15 is mounted on a conventional mobile stand (skid) 12 providing working clearance beneath the column tube 2. In a known manner, the top and bottom edges of the column tube wall 21 seal against respective downward and upward surfaces of the top and bottom flanges 22,25 with elastomeric sealing members 225,255 between. A discrete base plate 5 and top cap plate 3 close off the bottom and top ends of the tube. Like the top and bottom flanges, the base plate and top cap are of stainless steel. The base plate 5 is flat and fits sealingly—with the aid of a further elastomeric seal ring—against the underside of the bottom flange 25. It includes a central journal mounting for an inlet rotor structure 6, described later, and an offset slurry or drain hole 51 with a connector 511 beneath.

The top cap 3 is circular, like the base plate 5 and has a peripheral fixing flange 31 with a flat horizontal bottom surface 312 which fits down against the top fitting surface 221 of the upper flange 22 via a further elastomeric seal 38 which is held in compression between them.

The top cap 3 is generally conical in form, and has a central opening 32 incorporating a mounting 37 for an outlet structure 4 which includes an anti-vortex device 8 projecting down into the interior space of the interior or operating volume 15 of the column tube.

The drain hole 51 in the baseplate can be used for removing media slurry from the column, and conveniently also for putting it in so that the top cap 3 need not be removed for this.

The inlet structure 6 in this embodiment is provided by a rotor 61 with a hub 62 which communicates fluid input through the main inlet conduit 66 to the radially-extending arms 63 of the rotor. The arms are provided with one or more openings for the injection of fluid into the column. As is known, the entry holes in the rotor arms usually face downwardly. Inlet rotors of this kind are known. The number of arms is e.g. 2 to 10, more usually from 4 to 8. Usually both the buffer (or other fluidising liquid or vehicle) and the sample to be separated are introduced into the column by this route. The rotor is mounted against the underside of the base plate 5 by a mounting plate which carries beneath it a powered drive 65 to turn the rotor and a sealed bearing/union unit 68 beneath, where the rotating shaft conduit of the rotor meets the non-rotating inlet conduit 66 in a liquid-tight fashion. The drawing also shows one of a pair of cleaning conduits 67 for feeding pure water to wash and pressure-activate a rotary seal which acts between the rotor shaft and the base plate of the column to prevent liquid from escaping.

A rotary inlet structure of this kind is desirable, because it provides effective distribution of the sample and fluidising liquid across the area of the column, but other inlet structures may be used. Further, as is known, a perforated or mesh static distributor element may optionally be positioned in the column above the rotor (or other inlet structure) to distribute fluid flow and/or to retain the particles of the bed.

The top plate or top cap 3 is generally conical in form. In this embodiment it is machined from stainless steel, so that it can withstand substantial internal pressure. These components define the pressure envelope, and the system may be rated e.g. at 3 bar gauge pressure. The cap consists of an outer peripheral fixing flange 31, slightly thickened relative to the rest of the cap, defining a flat, radial, horizontal bottom fitting surface 312 which fits against the upward fitting surface 221 of the top flange 22. The top cap flange fitting surface 312 also defines an annular groove to house an elastomeric seal element 38. The flange has a circumferentially-distributed set of bolt holes, for clamping the top cap 3 down against the top flange 22 to seal the column closed. The bolt holes may correspond to the positions of the circumferentially-distributed tie rods 24. From the peripheral flange 31 inwards, the interior surface 35 of the top cap 3 defines a smooth upward cone at an angle of about 18 degrees (marked 8) up to the location of a central outlet structure 4. The outlet structure is connected on the outside of the cap 3 to an external outlet tube 7 and on the inner side of the cap to an axially-projecting vortex inhibitor 8, shown also in FIGS. 3 and 4.

In this process with a 600 mm internal diameter column, the angle of 18 degrees is found suitable for liquid flow to traverse radially inwardly over the flow surface 35 towards the outlet 4 and carry with it any air bubbles and cell debris rising to the top of the column so that they do not accumulate and interfere with the process.

FIG. 4 shows the outlet structure separately, having a mounting plate 41 by which it is bolted into the opening 32 of the cap 3 and an upwardly-projecting union 42 for securing the external outlet tube 7. This may be e.g. a tri-clamp joint. This steel part of the outlet unit defines a cylindrical axial outlet passage 43, and has an internal thread at its inner end. A vortex-inhibitor component 8 is threaded into this, by its own top external thread 85 (FIG. 4*b*). The vortex inhibitor 8 may be of engineering plastics such as PEEK. It has a top portion with a cylindrical outlet flow passage 43 continuing that of the steel outlet component above, an intermediate entrance portion having a set of three vanes 81, and a solid cylindrical nose 82 projecting axially down below the vanes 81 all the way to the bottom level of the cone. As seen in FIGS. 3 and 4 the vanes 81 divide the cylindrical flow outlet 43 into three radially-directed entrances 83, and project out beyond it—both radially and axially—into the column interior 15. The vanes 81 inhibit rotating (vortex) flow as the fluid enters the outlet. The nose portion 82 projects below into a region which, were a vortex to form approaching the outlet, would be occupied by the vortex. We find that by having a solid body occupying this space, vortex formation is further inhibited.

FIGS. 1 and 2 show the threaded fasteners 33 which hold the column top flange and top cap down through the tie rods 24. They also show two lifting eyes 333 which can be used to lift away the top cap safely.

In operation a bed of media particles (not shown) is loaded into the column interior via the port 51 and an upflow of buffer is established by feeding through the inlet 66 and into the column via the rotor 61. The rate of upflowing liquid is balanced against the loading of bed particles to expand the particle bed into a fluidised state, with the top surface of the bed stabilising at a level somewhat below, e.g. 70 to 100 mm below, the top edge of the cylindrical column tube (where it is visible through the transparent wall). The region above— the supernatant region—is filled with buffer liquid flowing to the outlet. The sample to be separated (e.g. a cell broth product) is fed into the bed separately or through the same inlet 66 as the buffer, either with buffer or alone, and passes up through the expanded bed of particles for adsorption of the target component. Cell debris and other unwanted substances can pass up through the bed space 15, between the fluidised particles, and out through the outlet 4 for collection. The vortex inhibitor 8 inhibits vortex formation in the liquid, and it is found that inhibiting vortices at the top of the column effectively inhibits vortex formation lower down as well, so that a stable particle bed can be maintained without voids or channelling.

When adsorption is finished the target substance can be removed from the media particles by the appropriate method, e.g. by loading with liquid at different pH, or with a different liquid, to elute the product. Again, this target substance-containing liquid can be pumped out through the top of the column if wished. When the bed of media particles is spent, it may be removed through the drain port 51.

The fixed top cap 3 can easily be removed for cleaning, enabling direct and ready access to the entire interior of the column tube for cleaning there.

Accordingly, the apparatus and method offer a convenience and simplicity which has not previously been available with expanded bed processes, because where the outlet flow has been regulated this has been by means of a piston which is complicated to control and can be difficult to clean.

Operating Example

A 250 litre, 600 mm ID, fixed bed height column as described above was used for production of a Mab.

Flow was always upflow, and air left the column easily. Elution was carried out in the fluidized mode without compression, avoiding the "channelling" which has bedevilled many earlier EBA processes using flow-regulating meshes, and allowing a fixed bed height design. Host cell proteins, DNA, cell debris and intact, viable cells were eluted before elution of the purified antibody.

The column has the 720 mm diameter conical top plate as described above, with three vanes at 120° in the anti-vortex outlet design and the nose of this extending down to just below the axial level of the start of the top cone convergence. Cone angle was 18°. The bottom inlet rotor had rotor arms with multiple injection ports directed down towards the base plate. This inlet device is very low shear, minimizing cell breakage.

High cell-density harvest material was applied directly to the fluidised bed under the following ranges:
Cell density: 60-160 million cells/mL (viability 99%)
Antibody titre: 1.34-12.5 g/L, cumulative titres 6-8 g/L over 21 days
DBC at ×2 expansion: 100 mg IgG/ml Protein A media, residence time 10-15 minute.
Load ratio: 20-22 g IgG/L settled bed
Overall Yield: >90%
Purity HP-SEC: >99.5%
Flow rate: 2,500 L/hr (500 cm/hr velocity).

DNA in the crude harvest load was 26,000,000 pg/ml by PCR, and in the eluate, 133 pg/ml giving a log 10 reduction of 5.3. The host cell protein in the crude harvest was 2,800 ug/ml by ELISA and 2 ug/ml in the eluate which is a log 10 reduction of 3.1

Eight ultrasound transceivers (sensors) mounted distributed up the side of the column tube were used to monitor the height of the fluidized bed. Liquid flow was adjusted via a control loop to maintain a constant bed height as reported by the ultrasound sensors. This is a 'process analytical technology' (PAT) in that live data are used to adjust the flow rate in real time and it can take into account concentration variations between fermentation cycles.

While the invention has been described above with reference to a specific example, the skilled person will understand that the concepts disclosed herein are generally applicable.

The invention claimed is:

1. Separation apparatus in the form of a chromatography column for expanded bed chromatography, the column having a top and a bottom and comprising:
   a vertical column tube having a cylindrical side wall and defining an operating space to contain a bed of particles for expanded bed chromatography in use;
   bottom inlet structure at the bottom of the column where process liquid, containing a cell culture product including insoluble solid material, enters the operating space and fluidises the bed of particles by upflow through the operating space; and
   a generally conical fixed cap plate fixed at the top of the column tube side wall to close off the top of the column, the fixed cap plate being exterior to the column tube, in that it does not extend or project inside the column tube side wall, the fixed cap plate having a peripheral fixing portion which is fixed around a top edge of the column tube side wall and has a downwardly-directed fitting surface, the column tube side wall having an upwardly-directed fitting surface, and said downwardly-directed fitting surface and said upwardly-directed fitting surface fitting together;
   the inner side of the fixed cap plate being an interior upwardly convergent flow surface facing onto the operating space and leading towards an outlet structure, the outlet structure being positioned centrally in the fixed cap plate, whereby said process liquid containing said insoluble solid material of the cell culture product flows up through the operating space and radially inwardly, in contact with the convergent flow surface of the fixed cap plate, from the periphery of the column tube to the outlet structure for the liquid and insoluble solid material to leave the operating space after passing through the bed of particles the convergence of the interior convergent flow surface being at an angle from 10° to 25° relative to horizontal.

2. Separation apparatus according to claim 1 in which the fixed cap plate is fixed to the column tube by threaded fasteners or clamps.

3. Separation apparatus according to claim 1 in which said downwardly- and upwardly-directed fitting surfaces are radial and perpendicular to an axis of the column tube.

4. Separation apparatus according to claim 1 in which the interior convergent flow surface of the fixed cap plate is convergent from the periphery of the fixed cap plate to the outlet structure.

5. Separation apparatus according to claim 1 in which the convergence of the interior convergent flow surface is conical.

6. Separation apparatus according to claim 1 in which the convergence of the interior convergent flow surface is at an angle from 15° to 20°.

7. Separation apparatus according to claim 1 in which the fixed cap plate consists essentially of a single conical piece comprising said peripheral fixing portion for fixing to the column tube around a top edge of the side wall thereof.

8. Separation apparatus according to claim 1 in which the outlet structure comprises a discrete conduit component fixed into the fixed cap plate.

9. Separation apparatus according to claim 1 in which the outlet structure comprises a formation for inhibiting rotational flow.

10. Separation apparatus according to claim 9 in which the formation for inhibiting rotational flow comprises one or more vanes extending both axially and radially.

11. Separation apparatus according to claim 9 in which the formation for inhibiting rotational flow projects below the convergent flow surface of the fixed cap plate, down into the operating volume.

12. Separation apparatus according to claim 9 in which the formation for inhibiting rotational flow is comprised in a vortex inhibitor structure having one or more vanes and a downwardly-directed axial nose portion below the level of said one or more vanes.

13. Separation apparatus according to claim 12 in which the vortex inhibitor structure extends down below the outlet structure at least to the axial position where the fixed cap plate begins to converge.

14. Separation apparatus according to claim 1 in which the bottom inlet structure defines an array of process liquid injection holes distributed across the column tube.

15. Expanded bed adsorption separation process carried out in separation apparatus according to claim 1, the method comprising:
provoding a bed of particulate medium in the operating space in the column tube;
causing a process liquid, the process liquid containing a cell culture product including insoluble solid material, to flow up through the column tube, from the bottom inlet structure to the outlet structure, through the bed of particulate medium with expansion of the bed;
causing said process liquid containing said insoluble solid material of the cell culture product, having flowed up through the operating space, to flow radially inwardly in contact over the convergent flow surface of the fixed cap plate from the periphery of the column tube to the outlet structure where the process liquid including said insoluble solid material leaves the operating space, and
separating a target substance from the process liquid by adsorption onto the media particles.

16. Separation apparatus in the form of a chromatography column for expanded bed chromatography, the column having a top and a bottom and comprising:
a vertical column tube having a cylindrical side wall and defining an operating space to contain a bed of particles for expanded bed chromatography in use, there being no mesh retainer for particles in the operating space at the top of the column;
bottom inlet structure at the bottom of the column for process liquid to enter the operating space and fluidise the bed of particles by upflow through the operating space;

a generally conical fixed cap plate fixed at the top of the column tube side wall to close off the top of the column, the inner side of the fixed cap plate being an interior upwardly convergent conical flow surface facing onto the operating space and leading towards an outlet structure defining an outlet opening, the outlet structure being positioned centrally in the fixed cap plate whereby said process liquid flows up through the operating space and radially inwardly, in contact with the convergent conical flow surface of the fixed cap plate, from the periphery of the column tube to the outlet structure for said liquid to leave the operating space through the outlet opening after passing through the bed of particles, the convergence of the interior convergent conical flow surface being at an angle from 10° to 25° relative to horizontal, and the outlet structure comprising a vortex inhibitor structure to inhibit rotational flow of said liquid leaving the operating space through the outlet opening, the vortex inhibitor structure comprising one or more vanes extending both axially and radially, and projecting down below the outlet opening into the operating space.

17. Separation apparatus according to claim 16 in which the vortex inhibitor structure comprises a downwardly-directed axial nose portion extending down below said one or more vanes.

18. Separation apparatus according to claim 16 in which the vortex inhibitor structure comprises a downwardly-directed axial nose portion extending down below the outlet opening at least down to the axial position where the fixed cap plate begins to converge upwardly.

19. Separation apparatus in the form of a chromatography column for expanded bed chromatography, the column having a top and a bottom and comprising:
a vertical column tube having a cylindrical side wall and defining an operating space to contain a bed of particles for expanded bed chromatography in use, there being no mesh retainer for particles in the operating space at the top of the column;
bottom inlet structure at the bottom of the column for process liquid to enter the operating space and fluidise the bed of particles by upflow through the operating space;
a generally conical fixed cap plate fixed at the top of the column tube side wall to close off the top of the column, the inner side of the fixed cap plate being an interior upwardly convergent conical flow surface facing onto the operating space and leading towards an outlet structure defining an outlet opening, the outlet structure being positioned centrally in the fixed cap component whereby said process liquid flows up through the operating space and radially inwardly, in contact with the convergent conical flow surface of the fixed cap plate, from the periphery of the column tube to the outlet structure for said liquid to leave the operating space through the outlet opening after passing through the bed of particles, the convergence of the interior convergent conical flow surface being at an angle from 10° to 25° relative to horizontal, and
the outlet structure comprising a vortex inhibitor structure to inhibit rotational flow of said liquid leaving the operating space through the outlet opening, the vortex inhibitor structure comprising:
one or more vanes extending both axially and radially, and projecting down below the outlet opening into the operating space, and a downwardly-directed axial nose portion extending down below the outlet opening at least down to the axial position where the fixed cap plate begins to converge upwardly.

* * * * *